(12) United States Patent
Notohardjono et al.

(10) Patent No.: US 11,648,133 B2
(45) Date of Patent: May 16, 2023

(54) LIQUID COOLING FOR MEDICAL DEVICES

(71) Applicant: INTERNATIONAL BUSINESS MACHINES CORPORATION, Armonk, NY (US)

(72) Inventors: Budy Notohardjono, Poughkeepsie, NY (US); Milnes P. David, New Paltz, NY (US); Roger R. Schmidt, Poughkeepsie, NY (US); Xiangfei Yu, Santa Clara, CA (US); Robert K. Mullady, Ulster, NY (US)

(73) Assignee: International Business Machines Corporation, Armonk, NY (US)

( * ) Notice: Subject to any disclaimer, the term of this patent is extended or adjusted under 35 U.S.C. 154(b) by 281 days.

(21) Appl. No.: 16/911,452

(22) Filed: Jun. 25, 2020

(65) Prior Publication Data

US 2021/0401593 A1    Dec. 30, 2021

(51) Int. Cl.
*A61F 2/72* (2006.01)
*A61F 2/80* (2006.01)
*F25B 21/02* (2006.01)
*A45F 3/16* (2006.01)
*A61F 2/70* (2006.01)
*A61F 2/50* (2006.01)
(Continued)

(52) U.S. Cl.
CPC .................. *A61F 2/72* (2013.01); *A45F 3/16* (2013.01); *A61F 2/80* (2013.01); *F25B 21/02* (2013.01); *A45F 2003/166* (2013.01); *A61F 2/742* (2021.08); *A61F 2/748* (2021.08); *A61F 2002/5081* (2013.01); *A61F 2002/701* (2013.01); *B25J 9/16* (2013.01); *G05B 15/02* (2013.01)

(58) Field of Classification Search
CPC .. A61F 2/72; A61F 2/742; A61F 2/748; A61F 2002/5081; A61F 2002/701; A61F 2/80; F25B 21/02; A45F 2003/166; B25J 9/16; G05B 15/02
See application file for complete search history.

(56) References Cited

U.S. PATENT DOCUMENTS

| 5,146,625 A | 9/1992 | Steele et al. |
| 5,421,326 A | 6/1995 | Rankin et al. |

(Continued)

FOREIGN PATENT DOCUMENTS

| WO | WO-2016090243 A1 * | 6/2016 | ............... B64G 1/50 |
| WO | 2017216151 A2 | 12/2017 | |
| WO | 2019039993 A1 | 2/2019 | |

OTHER PUBLICATIONS

Advent International Laird Connectivity, retrieved at: https://www.lairdtech.com/; downloaded May 19, 2020; 2 pgs.
(Continued)

*Primary Examiner* — Bruce E Snow
(74) *Attorney, Agent, or Firm* — Cantor Colburn LLP; Tihon Poltavets

(57) ABSTRACT

Embodiments include a cooling device for a medical device. The cooling device including a controller configured to receive data from one or more temperature sensors and a pump, configured to be operated by the controller, to circulate a cooling fluid through a cooling system and through fluid channels in the medical device. The cooling device is configured to be worn by a user and to be selectively coupled to the medical device by the user.

5 Claims, 7 Drawing Sheets

(51) Int. Cl.
*A61F 2/74* (2006.01)
*G05B 15/02* (2006.01)
*B25J 9/16* (2006.01)

(56) References Cited

U.S. PATENT DOCUMENTS

| | | | |
|---|---|---|---|
| 7,500,985 B2 | 3/2009 | Saadat | |
| 8,001,794 B2 * | 8/2011 | Windisch | F25B 21/02 62/3.5 |
| 9,814,607 B2 | 11/2017 | Zhe et al. | |
| 9,993,357 B2 | 6/2018 | Jonsson | |
| 2005/0246826 A1 | 11/2005 | McCarter et al. | |
| 2013/0103125 A1 | 4/2013 | Radspieler et al. | |
| 2015/0105865 A1 | 4/2015 | Davis et al. | |
| 2016/0067062 A1 * | 3/2016 | Jorgensen | A61F 2/7843 623/36 |
| 2017/0325975 A1 | 11/2017 | Leroy et al. | |
| 2021/0369498 A1 * | 12/2021 | Costello | A61F 7/02 |

OTHER PUBLICATIONS greylor.com "Greylor" pump; retrieved at: https://www.greylor.com/; downloaded May 19, 2020; 9 pgs.

Koolance "ALR-4500" Liquid Cooling Solutions, retrieved at: https://koolance.com/; downloaded May 19, 2020; 2 pgs.

Pace, Eileen "Vet's Self-Cooling Prosthetic Could Help Amputees Beat The Heat", retrieved at: https://www.npr.org/2014/11/11/363313691/vets-self-cooling-prosthetic-could-helpamputees-beat-the-heat; dated Nov. 11, 2014; 6 pgs.

Rogers Corporation "curamik ADVANTAGE features to customize your substrates" retrieved at: http://www.curamik.com/index.aspx; downloaded May 19, 2020; 4 pgs.

* cited by examiner

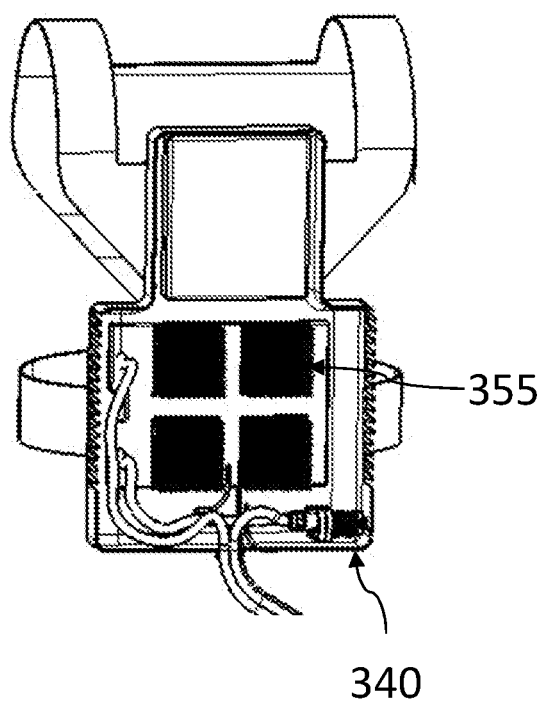
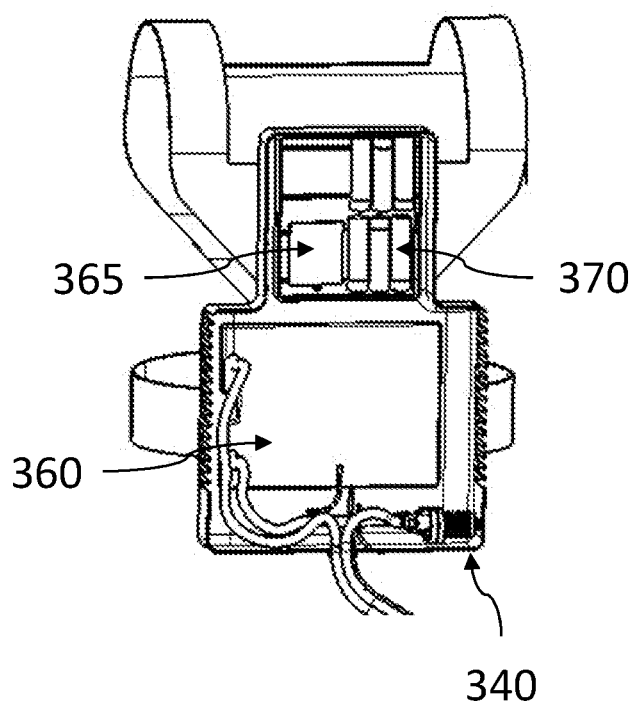
FIG. 3C
FIG. 3D

LIQUID COOLING FOR MEDICAL DEVICES

BACKGROUND

The present invention generally relates to medical devices, and more specifically, to liquid cooling for medical device.

A medical device such as, a prosthetic implant, is an artificial device that replaces a missing body part, which may be lost through trauma, disease, or a condition present at birth. Prosthetics are intended to restore the normal functions of the missing body part. In general, heat and perspiration at the point at which the prosthetic attached to the user are some of the biggest complaints expressed by the users of prostheses.

SUMMARY

Embodiments of the present invention are directed to a method for providing liquid cooling for a medical device. A non-limiting example of the computer-implemented method includes receiving, by a controller, temperature data from one or more temperature sensors in the medical device and determining a skin temperature of a stump in the medical device based on the temperature data. The method also includes activating a cooling device based on a determination that the skin temperature is above a first threshold level. The method further includes deactivating the cooling device based on a determination that the skin temperature is below a second threshold level. The cooling device is configured to be worn by a user and to be selectively coupled to the medical device by the user.

Embodiments of the present invention are directed to a system for liquid cooling for a medical device. A non-limiting example of the system a cooling device for a medical device includes a controller configured to receive data from one or more temperature sensors and a pump, configured to be operated by the controller, to circulate a cooling fluid through a cooling system and through fluid channels in the medical device. The cooling device is configured to be worn by a user and to be selectively coupled to the medical device by the user.

Embodiments of the invention are directed to a computer program product for providing liquid cooling for a medical device, the computer program product comprising a computer readable storage medium having program instructions embodied therewith. The program instructions are executable by a processor to cause the processor to perform a method. A non-limiting example of the method includes receiving, by a controller, temperature data from one or more temperature sensors in the medical device and determining a skin temperature of a stump in the medical device based on the temperature data. The method also includes activating a cooling device based on a determination that the skin temperature is above a first threshold level. The method further includes deactivating the cooling device based on a determination that the skin temperature is below a second threshold level. The cooling device is configured to be worn by a user and to be selectively coupled to the medical device by the user.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIGS. 3A, 3B, 3C, and 3D depict schematic diagrams of a system for liquid cooling a medical device in accordance with an embodiment;

The diagrams depicted herein are illustrative. There can be many variations to the diagram, or the operations described therein without departing from the spirit of the invention. For instance, the actions can be performed in a differing order or actions can be added, deleted or modified. Also, the term "coupled", and variations thereof describes having a communications path between two elements and does not imply a direct connection between the elements with no intervening elements/connections between them. All these variations are considered a part of the specification.

DETAILED DESCRIPTION

Turning now to an overview of the aspects of the invention, one or more embodiments of the invention provide a system for liquid cooling a medical device, such as a prosthetic device. In exemplary embodiments, the system is configured to cool the skin at the junction of the human body and a prosthetic device. The system is further configured to lower and maintain skin temperature within the prosthetic to a comfortable level during heightened levels of user physical activity. By lowering skin temperature, the system is able to reduce perspiration around the stump which can often cause additional discomfort to the user.

Although primarily discussed as being applied to prosthetic devices, the methods and systems described herein are not limited to being used with prosthetic devices and it will be appreciated by those of ordinary skill in the art that the methods and systems described herein can be used with any device that is placed on the skin to regulate the temperature of the skin at the interface of the device with the skin. For example, the methods and systems described herein can be used to regulate the temperature of the skin of a user wearing an exoskeleton device or a medical device other than a prosthetic device.

Figure 1:
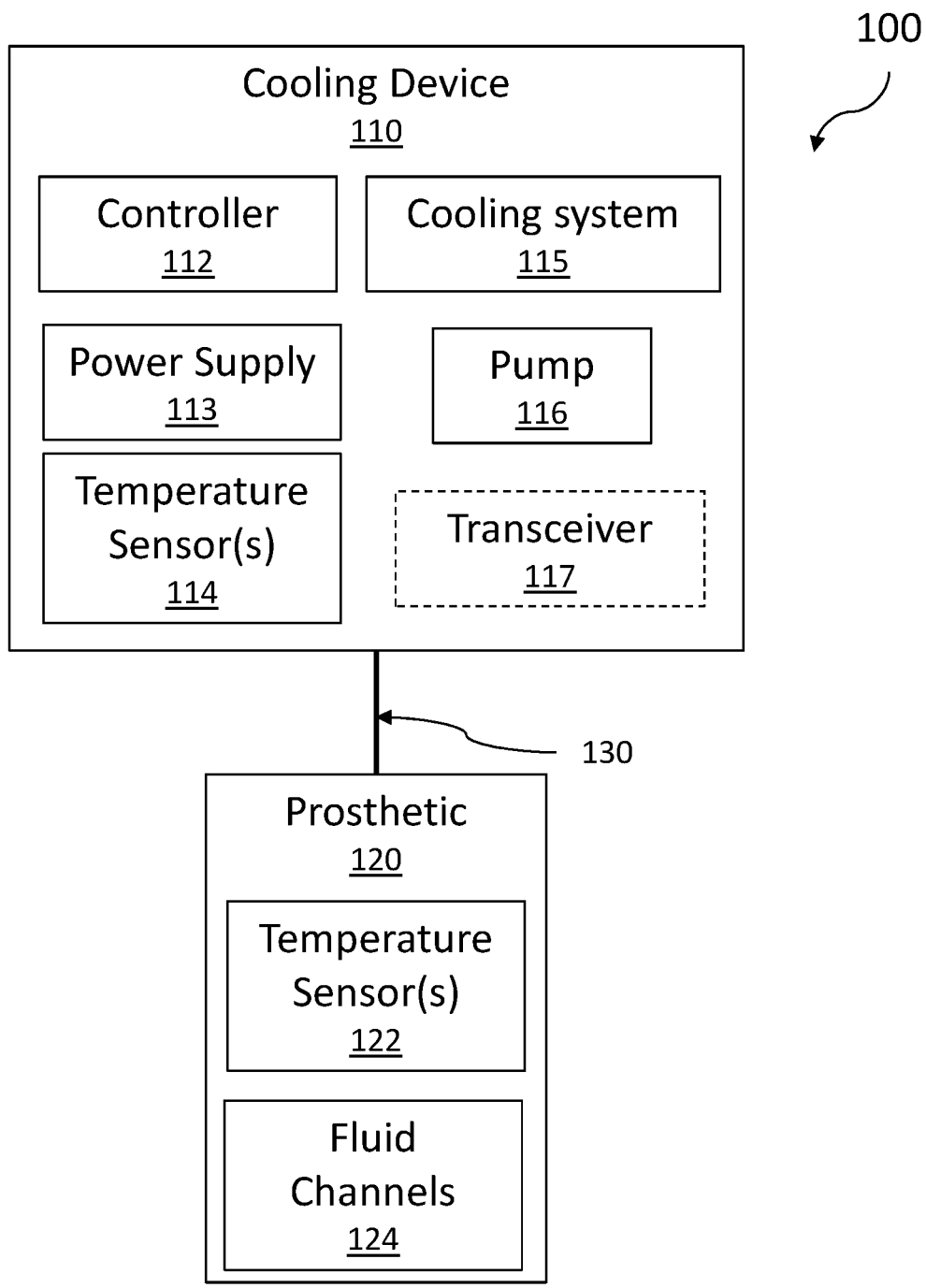
FIG. 1 depicts a block diagram of a system for liquid cooling a medical device in accordance with an embodiment.

Referring now to FIG. 1, a block diagram of a system 100 for liquid cooling a prosthetic device in accordance with an embodiment is shown. The system 100 includes a cooling device 110 that is coupled to a prosthetic 110 by tubing 130.

In exemplary embodiments, the tubing is removable attached to one or more of the cooling device 110 and the prosthetic 110. The prosthetic 110 includes one or more temperature sensors 122 that are configured to measure the temperature of the skin of a body part disposed in the prosthetic 110. The prosthetic 110 also includes a plurality of fluid channels 124 that are disposed within the body of the prosthetic 110. The fluid channels 124 are configured to receive a fluid from the cooling device 110 via the tubing 130. In exemplary embodiments, the fluid channels 124 are disposed on an inner surface of the prosthetic 110 and are in direct contact with the liner. In one embodiment, the fluid channels are at least partially made of copper tubes that are thick-walled and will not reduce the mechanical strength of the socket of the prosthetic 110.

In exemplary embodiments, the cooling device 110 includes a controller 112, a power supply 113, one or more temperature sensors 114, a cooling system 115, a pump 116, and a transceiver 117. In one embodiment, the controller 112 includes one of a field-programmable gate arrays (FPGAs), an application-specific integrated circuit (ASIC), and a general-purpose processor that is configured to control the operation of the cooling device 110. The power supply 113 includes one or more energy storage means, such as a battery that provides power to the cooling device 110. The temperature sensors 114 are configured to monitor one or more of the temperature of the air surrounding the cooling device, a temperature of the fluid being supplied to the prosthetic 110, and the temperature of the fluid being received from the prosthetic 110. The pump 116 is configured to circulate the fluid between the cooling system 115 of the cooling device 110 and the prosthetic 110. In one embodiment, the transceiver 117 is configured to facilitate communication between the cooling device 110 and the temperature sensors 122 of the prosthetic 110. In another embodiment, the transceiver 117 is configured to facilitate communication between the cooling device 110 and a separate computing device (not shown) such as a smartphone, tablet, or personal computer.

In exemplary embodiments, the cooling system 115 is configured to receive a fluid and reduce the temperature of the cooling fluid. In one embodiment, the cooling system 115 includes one or more of a cold plate that includes a plurality of channels for the cooling fluid, one or more heat sink disposed on the cold plate, and one or more fans to circulate air over the heat sink. In exemplary embodiment, the cold plate and heat sinks are made of one or more of aluminum, copper, or other such material. In one embodiment, the cooling system 115 also includes a thermoelectric cooling module (TEM) that is also used to reduce the temperature of the cooling fluid. In exemplary embodiments, the TEM is selectively activated based on the detected temperature in the socket, the temperature of the cooling fluid, and the air temperature.

Figure 2:
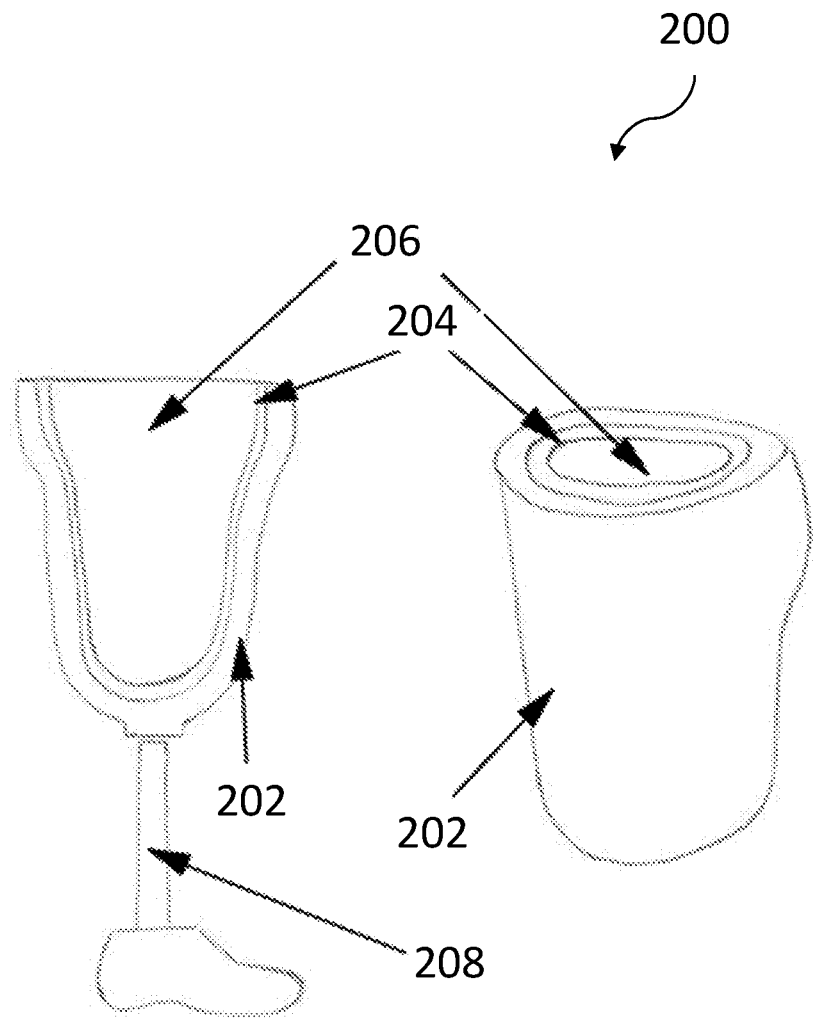
FIG. 2 depicts a schematic of a prosthetic device in accordance with an embodiment.
Figures 3A, 3B:
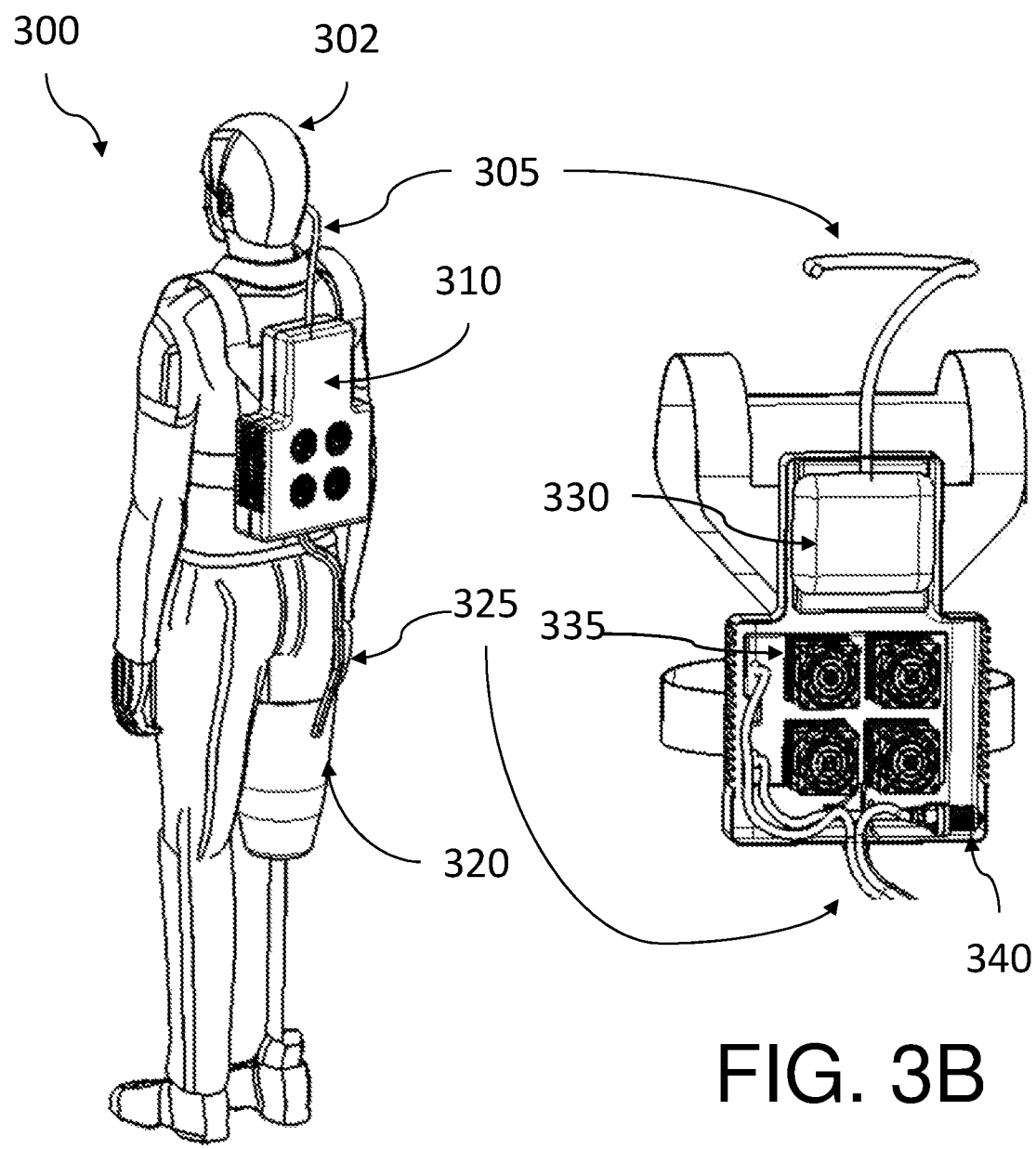

FIG. 2 generally illustrates a prosthetic device 200 that includes a rigid body 202 that includes a liner 204. The prosthetic device 200 also includes a socket 206 that is configured to receive a body part of a user, also referred to herein as a stump. Depending on the type of prosthetic, the prosthetic device 200 may include a rod 208 or other attachment affixed to the rigid body 202. As discussed above, heat and perspiration at the point at which the prosthetic device 200 attaches to a user are common complaints expressed by the users of prosthetic devices 200.

Referring now to FIGS. 3A, 3B, 3C, and 3D schematic diagrams of a system 300 for liquid cooling a prosthetic device 320 in accordance with an embodiment. As illustrated, the system 300 includes a cooling device 310 that is worn by a user 302. The cooling device is connected to the prosthetic device 320 via tubing 325. In exemplary embodiments, the cooling device includes a water reservoir 330 and a tube 305 that is configured to allow the user to drink water from the water reservoir. In one embodiment, the cooling system is configured to keep the water in the water reservoir 330 below a desired maximum temperature set by the user. The cooling device 310 includes a pump 340 that is configured to circulate a cooling fluid through a cooling plate 360. In one embodiment, a plurality of heat sinks 355 are disposed on the cooling plate 360 and fans 335 are configured to circulate air across the heat sinks 355.

In one embodiment, the tubing 325 is made of plastic and can optionally include a conductive material to facilitate communications between sensors in the prosthetic device 320 and the cooling device 310. In another embodiment, the cooling device 310 is configured to wirelessly communicate with the sensors in the prosthetic device 320. The cooling device 310 further includes a power supply 370 and a controller 365.

Figure 4A:
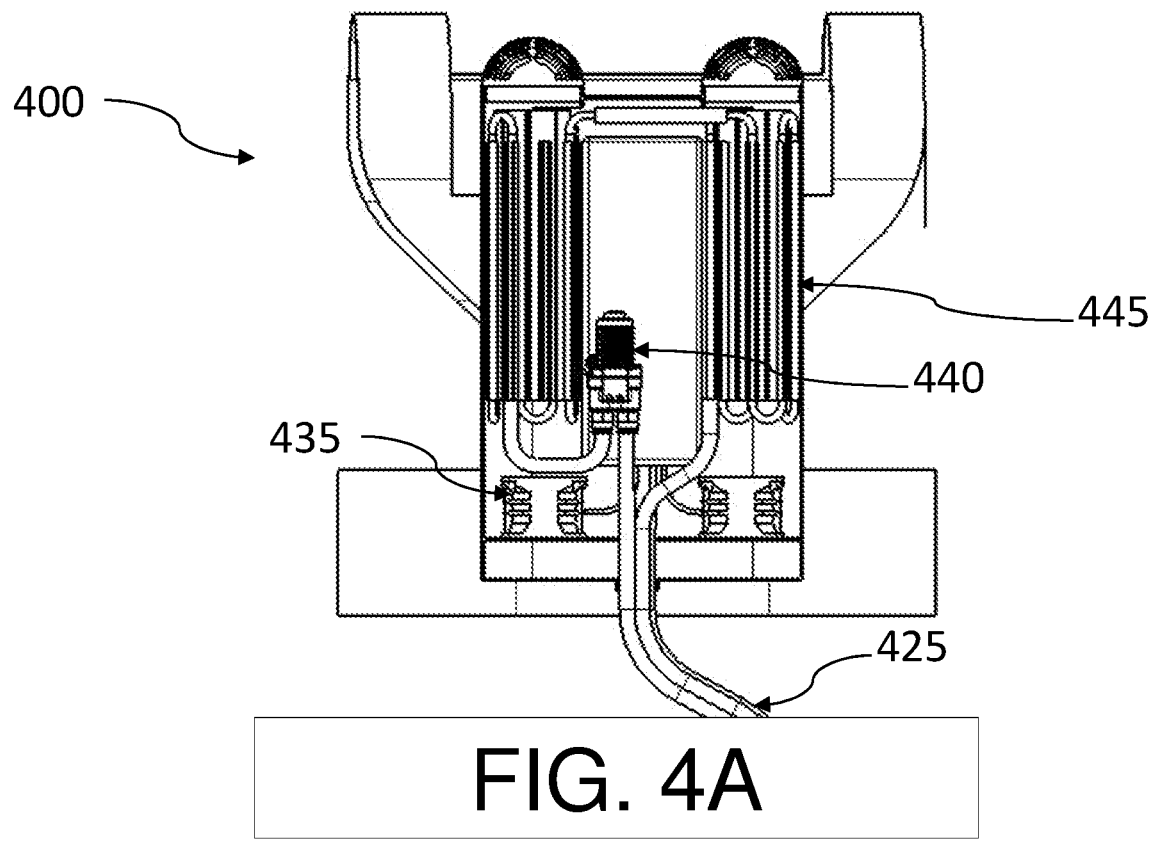
FIGS. 4A and 4B depict schematic diagrams of a system for liquid cooling a medical device in accordance with another embodiment.
Figure 4B:
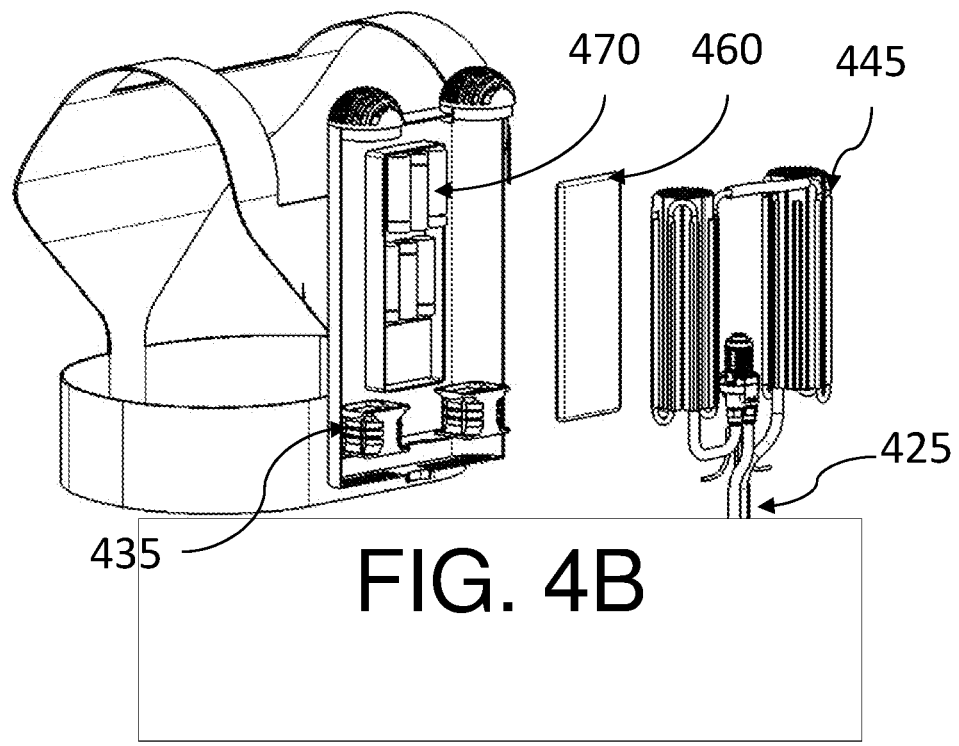

Referring now to FIGS. 4A and 4B schematic diagrams of a cooling device 410 for liquid cooling a prosthetic device in accordance with another embodiment are shown. The cooling device 410 is generally similar to the system 310 shown in FIGS. 3A, 3B, and 3C, however, the cooling device 410 has a different configuration. The cooling device 410 includes fans 435, a pump 440, metal tubing 445, a power supply cover plate 460, a power supply 470, and plastic tubing 425. In exemplary embodiments, the pump 440 circulates a cooling fluid through the metal tubing 445 attached to the cooling fins to reduce the temperature of the cooling fluid and provides the cooling fluid to the prosthetic device via plastic tubing 425.

Figure 5A:
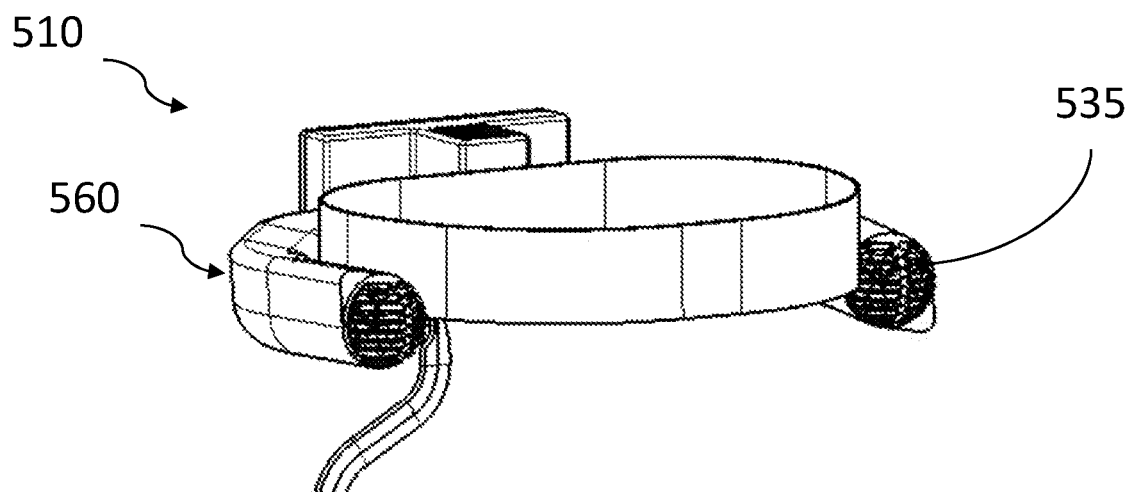
FIGS. 5A and 5B depict schematic diagrams of a system for liquid cooling a medical device in accordance with a further embodiment.
Figure 5B:
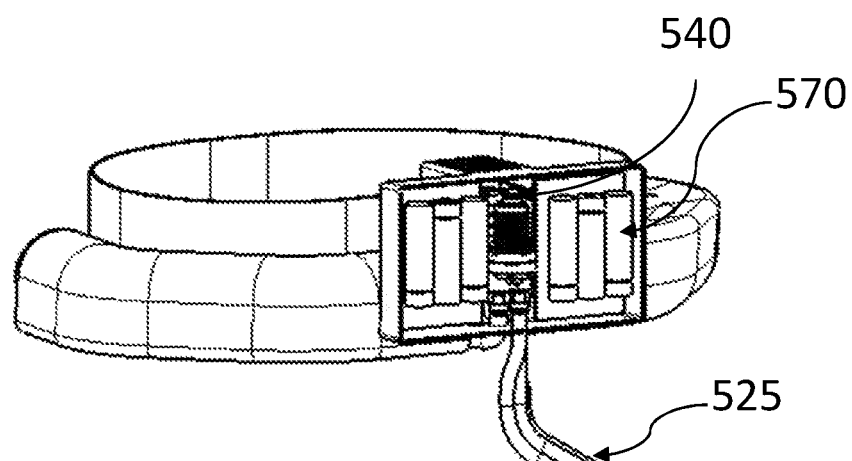

Referring now to FIGS. 5A and 5B schematic diagrams of a cooling device 510 for liquid cooling a prosthetic device in accordance with a further embodiment are shown. The cooling device 510 is generally similar to the system 310 shown in FIGS. 3A, 3B and 3C, however, the cooling device 510 has a different configuration and is designed to be worn around the waist of a user rather than over the user's upper torso. The cooling device 510 includes fans 535, a pump 540, a power supply 570, and plastic tubing 525. The cooling device 510 also includes a metal tubing (not shown) and a cooling fins (not shown) disposed within a housing 560. In exemplary embodiments, the pump 540 circulates a cooling fluid through the metal tubing to reduce the temperature of the cooling fluid and provides the cooling fluid to the prosthetic device via plastic tubing 525.

Figure 6:
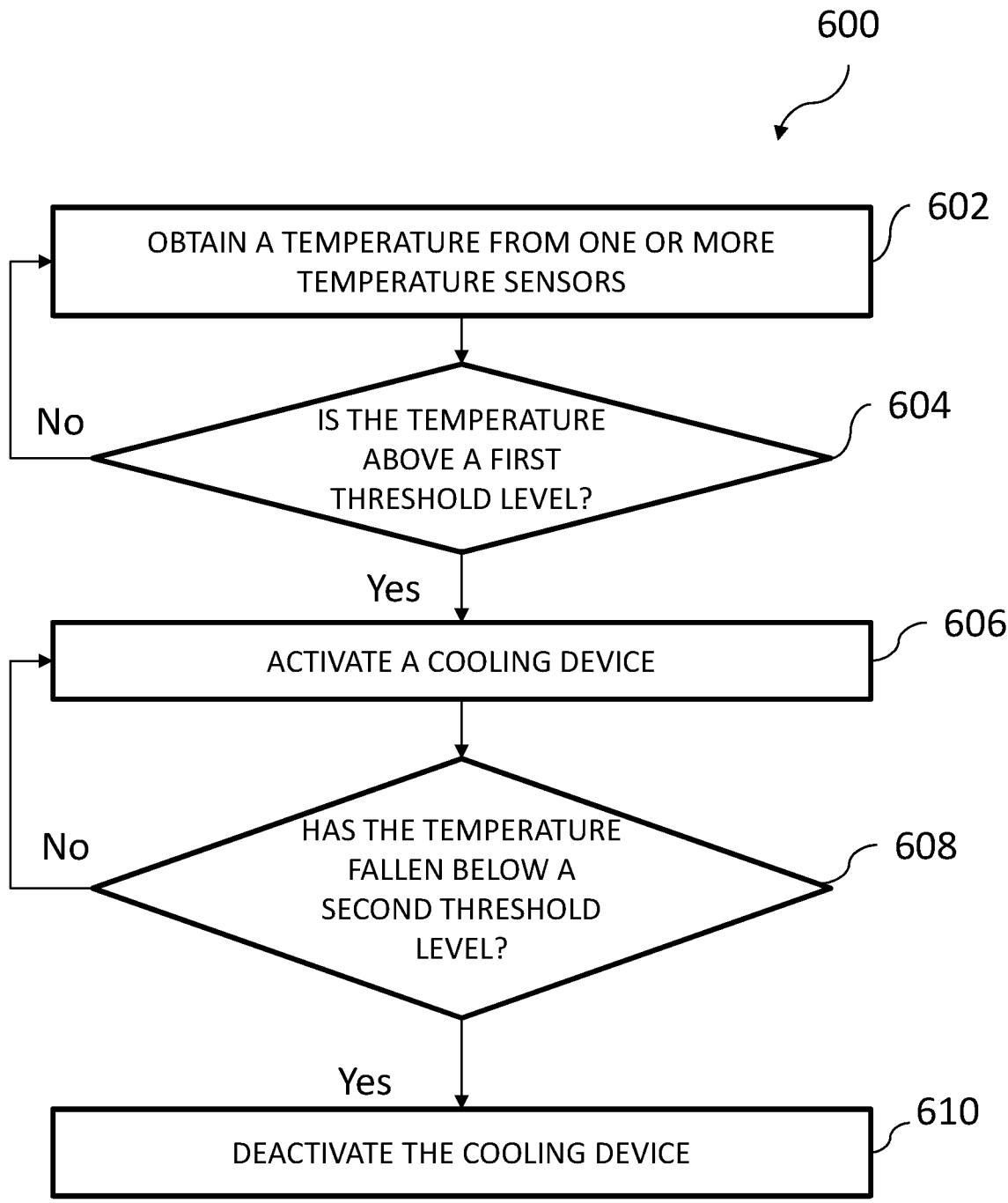
FIG. 6 depicts a flow chart of a method for liquid cooling a medical device in accordance with an embodiment.

Referring now to FIG. 6 a flow chart of a method 600 for liquid cooling a prosthetic device in accordance with an embodiment is shown. The method 600 begins at block 602 by obtaining a temperature from one or more temperature sensors. In exemplary embodiments, the one or more temperature sensors include one or more of a skin temperature sensor, disposed in the prosthetic device, an air temperature sensor, a temperature sensor disposed in the cooling device, and a temperature sensor disposed in the tubing connecting the cooling device to the prosthetic device. Next, as shown at decision block 604, the method 600 includes determining whether a temperature reading from one of the one or more sensors is above a first threshold level. For example, is the temperature of the skin of the stump in the prosthetic device above 34° C. (93.2 F). If the temperature reading of the one of the one or more sensors is above a first threshold level, the method 600 proceeds to block 606 and activates or adjusts a cooling device. Otherwise, the method 600 returns to block 602.

Next, as shown at decision block 608, it is determined if the temperature that had exceeded the first threshold level has fallen below a second threshold level. For example, is the temperature of the skin of the stump in the prosthetic device below 32° C. (89.6 F). If the temperature that had exceeded the first threshold level has fallen below a second threshold level, the method 600 proceeds to block 610 and deactivates or readjusts the cooling device. Otherwise, the method 600 returns to block 606 and continues to cool the prosthetic device.

In exemplary embodiments, the prosthetic device includes a plurality of temperature sensors disposed within the prosthetic device, and determining the temperature of the skin of the stump in the prosthetic device includes taking an average of the temperature readings from the plurality of temperature sensors.

In exemplary embodiments, the cooling device is configured to be operated at various levels that provide different amounts of cooling based on the temperature readings from the one or more temperature sensors. For example, if the air temperature is above a threshold level, a thermoelectric cooling module (TEM) is selectively activated. However, if the air temperature is below a different threshold level the cooling device can be operated without the TEM being activated. Furthermore, the speed of operation of the pumps and fans of the cooling device, as well as valve position on a bypass valve installed in the cooling fluid loop, can all be controlled based on the temperature readings from the one or more temperature sensors.

In exemplary embodiments, the cooling device is configured to maintain a desired temperature of the prosthesis under the various operating conditions for a reasonable period of time. In one embodiment, the desired temperature has a default value of 33° C. (91.4 F) and the desired temperature can be changed by the user. In one embodiment, the transceiver of the cooling device is configured to communicate with an electronic device such as a smartphone, tablet or personal computer that can be used to set the desired temperature and to set other desired operating conditions of the cooling device.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method for cooling a medical device, the method comprising:
    receiving, by a controller, temperature data from one or more temperature sensors in the medical device;
    determining a skin temperature of a stump in the medical device based on the temperature data;
    based on a determination that the skin temperature is above a first threshold level, activating a cooling device; and
    based on a determination that the skin temperature is below a second threshold level, which is lower than the first threshold level, deactivating the cooling device, wherein the cooling device is configured to be worn by a user and to be selectively coupled to the medical device by the user, and wherein the one or more temperature sensors are disposed within the medical device, and wherein the cooling device is selectively coupled to the medical device by a plastic tubing that fluidly connects the cooling system to fluid channels in the medical device and the plastic tubing includes a conductive material used to provide data from at least one of the one or more temperature sensors disposed in the medical device to the controller.

2. The method of claim 1, wherein the cooling device includes a cooling plate, one or more heat sinks disposed on the cooling plate and one or more fans configured to circulate air across the heat sinks.

3. The method of claim 2, wherein the cooling device further comprises a thermoelectric cooling module.

4. The method of claim 1, wherein the one or more temperature sensors include at least two temperature sensors, determining the skin temperature of the stump in the medical device includes averaging the temperature data from each of the at least two temperature sensors in the medical device.

5. A method for cooling a medical device, the method comprising:
 receiving, by a controller, temperature data from one or more temperature sensors in the medical device;
 determining a skin temperature of a stump in the medical device based on the temperature data;
 based on a determination that the skin temperature is above a first threshold level, activating a cooling device;
 based on a determination that the skin temperature is below a second threshold level, which is lower than the first threshold level, deactivating the cooling device,
 wherein the cooling device is configured to be worn by a user and to be selectively coupled to the medical device by the user, and wherein the one or more temperature sensors are disposed within the medical device;
 receiving, by the controller, air temperature data from one or more air temperature sensors; and
 based on a determination that the cooling device is active, controlling an operating condition based on the air temperature data.

* * * * *